United States Patent [19]
Wang

[11] Patent Number: 6,061,585
[45] Date of Patent: May 9, 2000

[54] METHOD AND APPARATUS FOR DETECTING CHARGED PARTICLES IN AN AQUEOUS SOLUTION

[75] Inventor: Wei Kung Wang, 61-3-14, Section 2, Yen-Chu-yun Rd., Taipei, Taiwan, 115

[73] Assignee: Wei Kung Wang, Taipei, Taiwan

[21] Appl. No.: 08/901,532

[22] Filed: Jul. 28, 1997

Related U.S. Application Data

[63] Continuation-in-part of application No. 08/563,006, Nov. 27, 1995, abandoned.

[51] Int. Cl.$^7$ .......................................................... A61B 5/00
[52] U.S. Cl. ............................................ 600/345; 600/547
[58] Field of Search ..................................... 600/345–353, 600/547

[56] References Cited

U.S. PATENT DOCUMENTS

| | | | |
|---|---|---|---|
| 4,927,502 | 5/1990 | Raeding et al. | 600/345 |
| 5,220,920 | 6/1993 | Gharib | 600/345 |
| 5,250,419 | 10/1993 | Bernard et al. | 600/345 |
| 5,806,517 | 9/1998 | Gerhardt et al. | 600/345 |

OTHER PUBLICATIONS

Pertinent pages of *Electrode Kinetics* by John Albery, Oxford University press, 1975 are provided and is described on p. 1 in the Background of Title Invention section of the present application.

Pertinent pages of *Electrodes and the Measurement of Bioelectric Events* by L.A. Geddes, Willey–interscience, 1972 are provided and is described on p. 1 in the Background of Title Invention section of the present invention.

*Primary Examiner*—Robert L. Nasser

[57] ABSTRACT

A method of detecting the charged particles in an aqueous solution, including immersing one of two electrodes in the aqueous solution to provide a conductive path between the aqueous solution and the other electrode; applying a stepping potential through the electrodes to measure an impulse current through the aqueous solution; and comparing the measured impulse current with an impulse current of a reference solution having known ingredients to determine if the two solutions are similar.

4 Claims, 5 Drawing Sheets

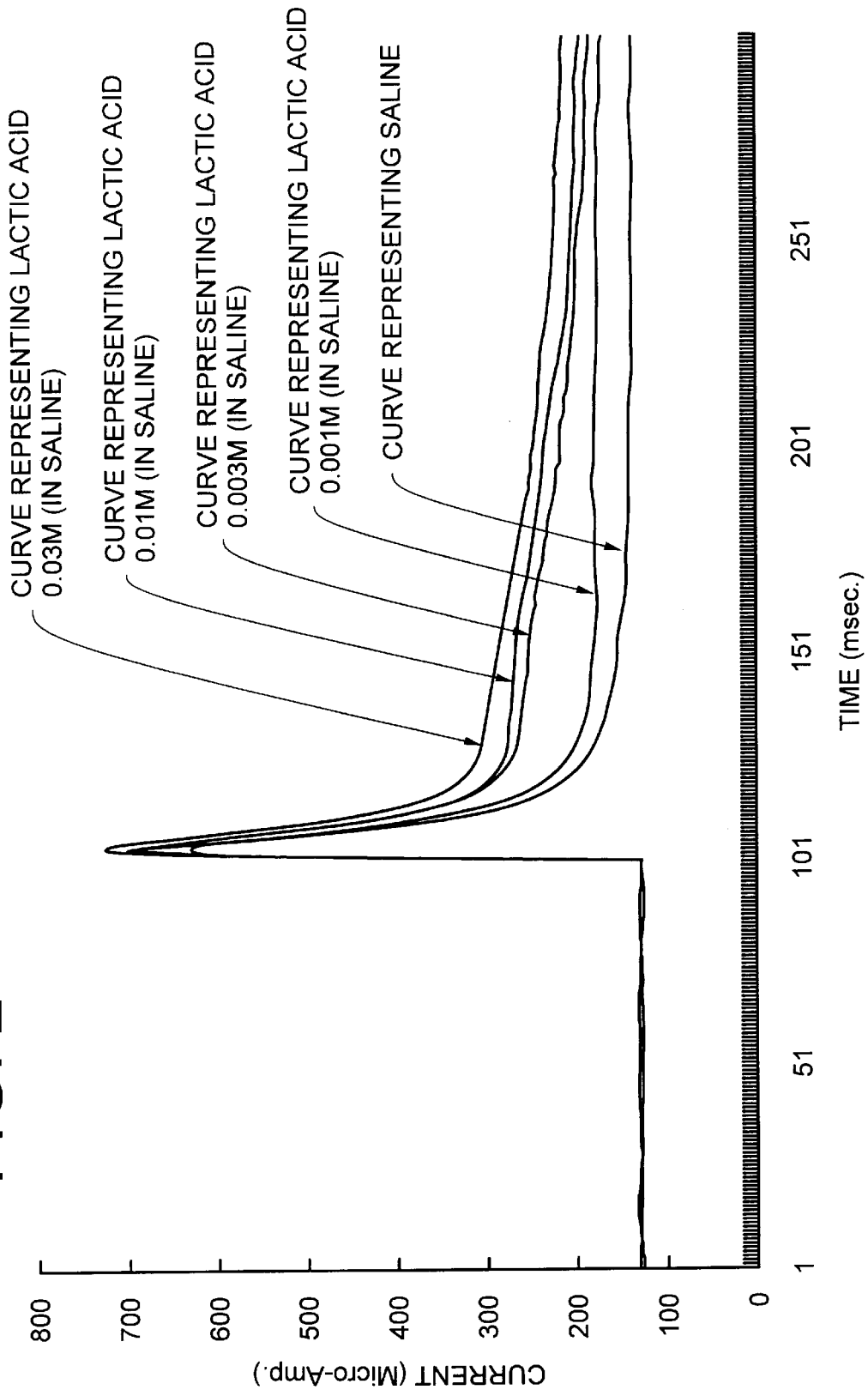

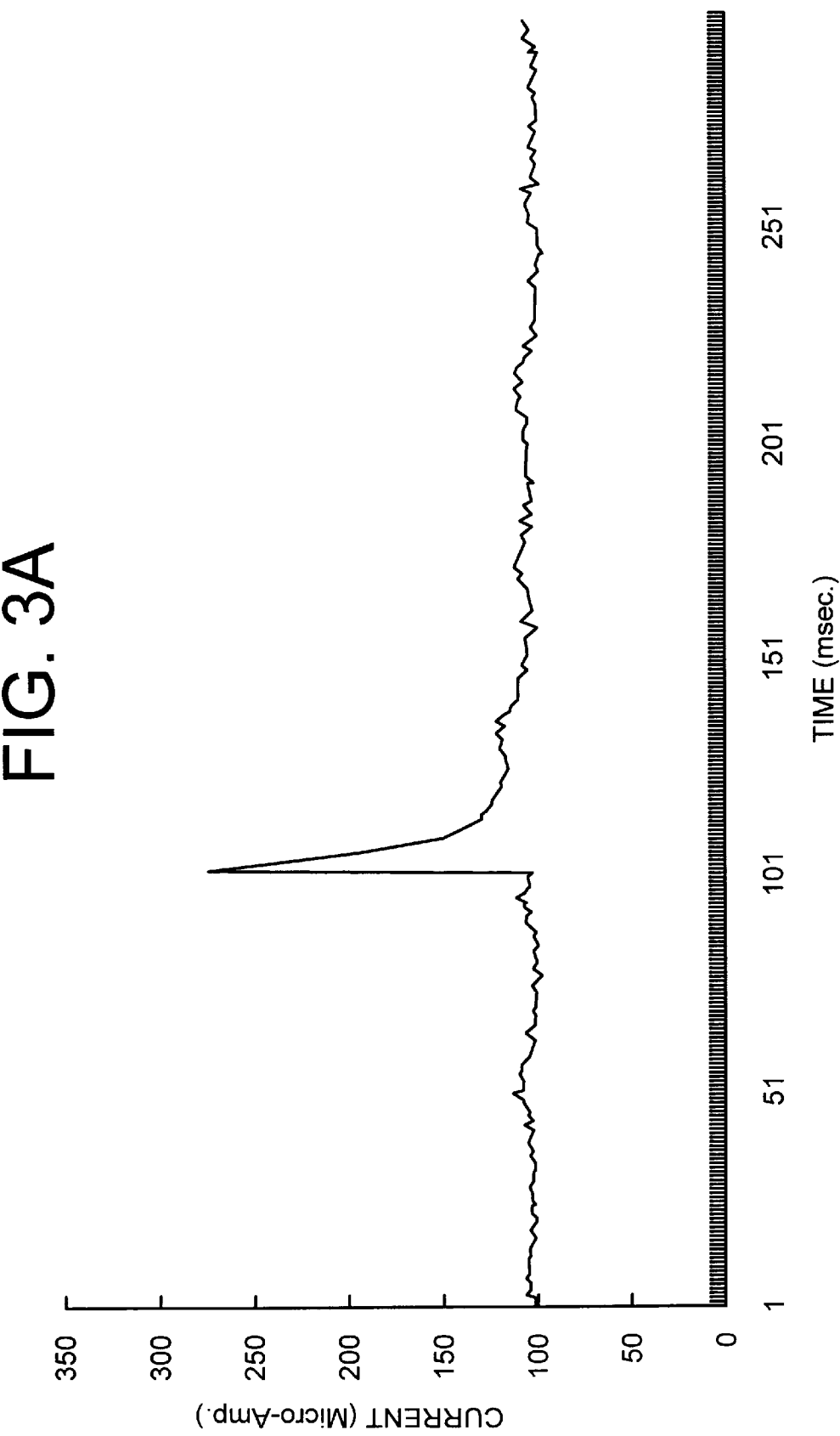

METHOD AND APPARATUS FOR DETECTING CHARGED PARTICLES IN AN AQUEOUS SOLUTION

This application is a continuation-in-part of application Ser. No. 08/563,006 filed on Nov. 27, 1995, now abandoned the entire contents of which are hereby incorporated by reference.

BACKGROUND OF THE INVENTION

The present invention relates to a method and apparatus for detecting charged particles in an aqueous solution, in which electrodes are immersed by supplying a stepping potential and measuring the induced impulse current. Most studies on electrodes in the past were made during steady state, such as the measurement of the H+ and other ions, or the electrical signal measurement. These studies focused on ways to eliminate the transient response to the electrodes for EKG (electrocardiogram) or EEG (electro-encephalogram), which depends on the ingredient of the surrounding solution, as described in Electrode Kinetics by John Albery, Oxford University press, 1975 and Electrodes and the Measurement of Bioelectric Events by L. A. Geddes, Wiley-interscience, 1972.

SUMMARY OF THE INVENTION

The present invention aims to use the transient state, which has long been neglected, to analyze charged particles in a solution where the electrodes are immersed. A water molecule is a strange particle which has a very large dipole. In the aqueous solution, ions, radicals or charged particles are surrounded by the dipole water molecules to form aggregates. These aggregates have different moving and rotational properties according to the ions, radicals or charged colloid particles in the center thereof.

According to the present invention, there is provided a method for detecting the charged particles in an aqueous solution, which comprises the steps of: supplying a stepping potential; and measuring the induced impulse current, so that the different charged particles can be distinguished from each other if there are specific impulse currents for them due to different sizes, shapes, or concentrations of the ions, radicals or charged colloid particles.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2 is a graph illustrating the different curves based on the transient response used in accordance with the present invention and representing Lactic Acid 0.03M, Lactic Acid 0.01M, Lactic Acid 0.003M, Lactic Acid 0.001M in saline and only saline;

FIGS. 3A and 3B are graphs illustrating the different curves based on the transient response used in accordance with the present invention and representing tissue with normal blood circulation and tissue with poor circulation.

Further scope of applicability for the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 4:
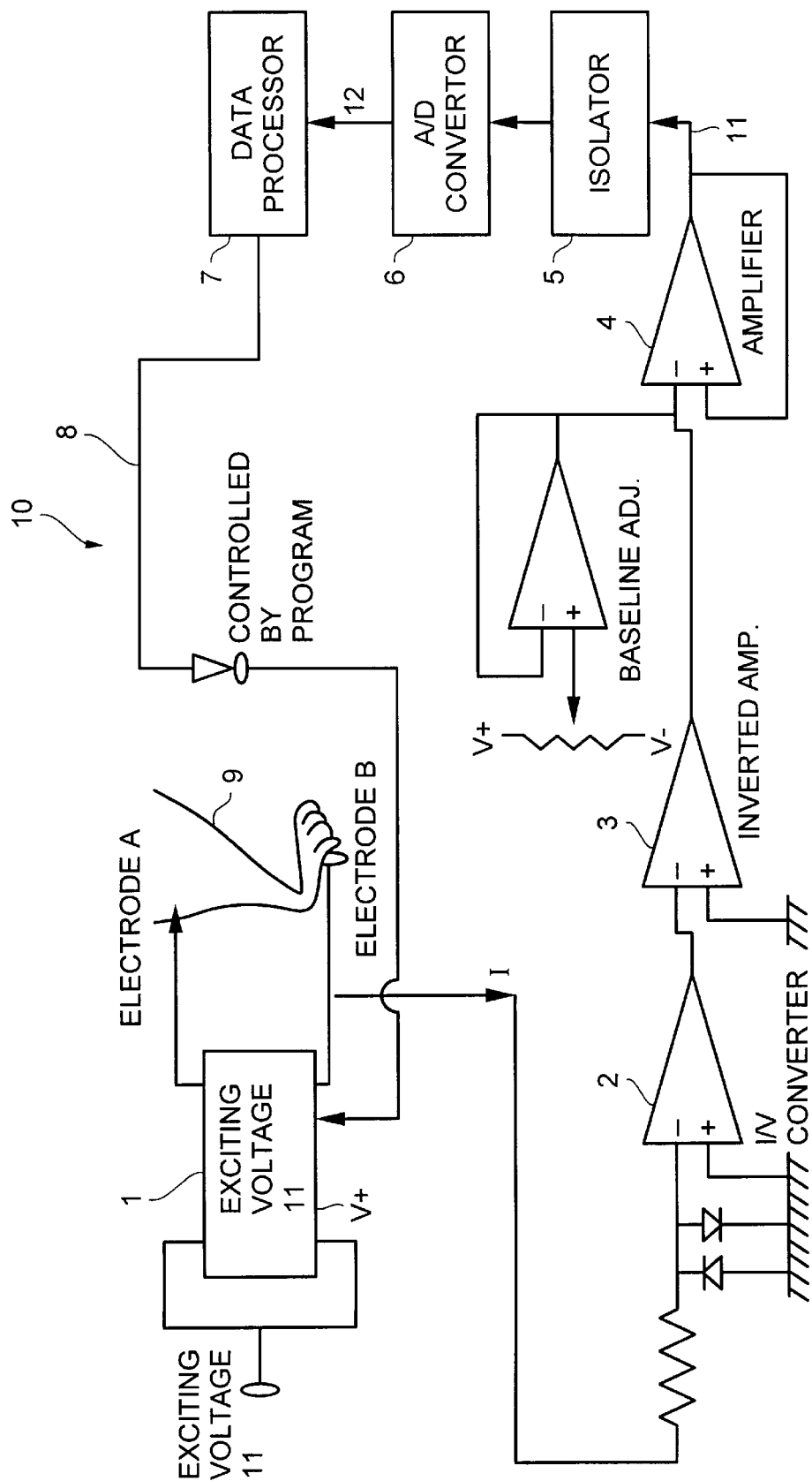
FIG. 4 is a schematic diagram of the apparatus in another preferred embodiment of the present invention.

Referring to FIG. 4, the method of detecting charged particles in an aqueous solution according to the present invention comprises the steps of: (a) immersing a pair of electrodes (A and B in FIG. 4) in the solution; (b) applying a stepping potential through the electrodes A and B to measure an impulse current through the solution; and (c) comparing the impulse current with an impulse current of another solution having known ingredients to determine if they are similar to each other. In a preferred embodiment, the above aqueous solution is in a biological body. One of the electrodes A includes a needle for penetrating into tissue of the biological body in order to detect a solution inside the tissue.

Figure 3B:
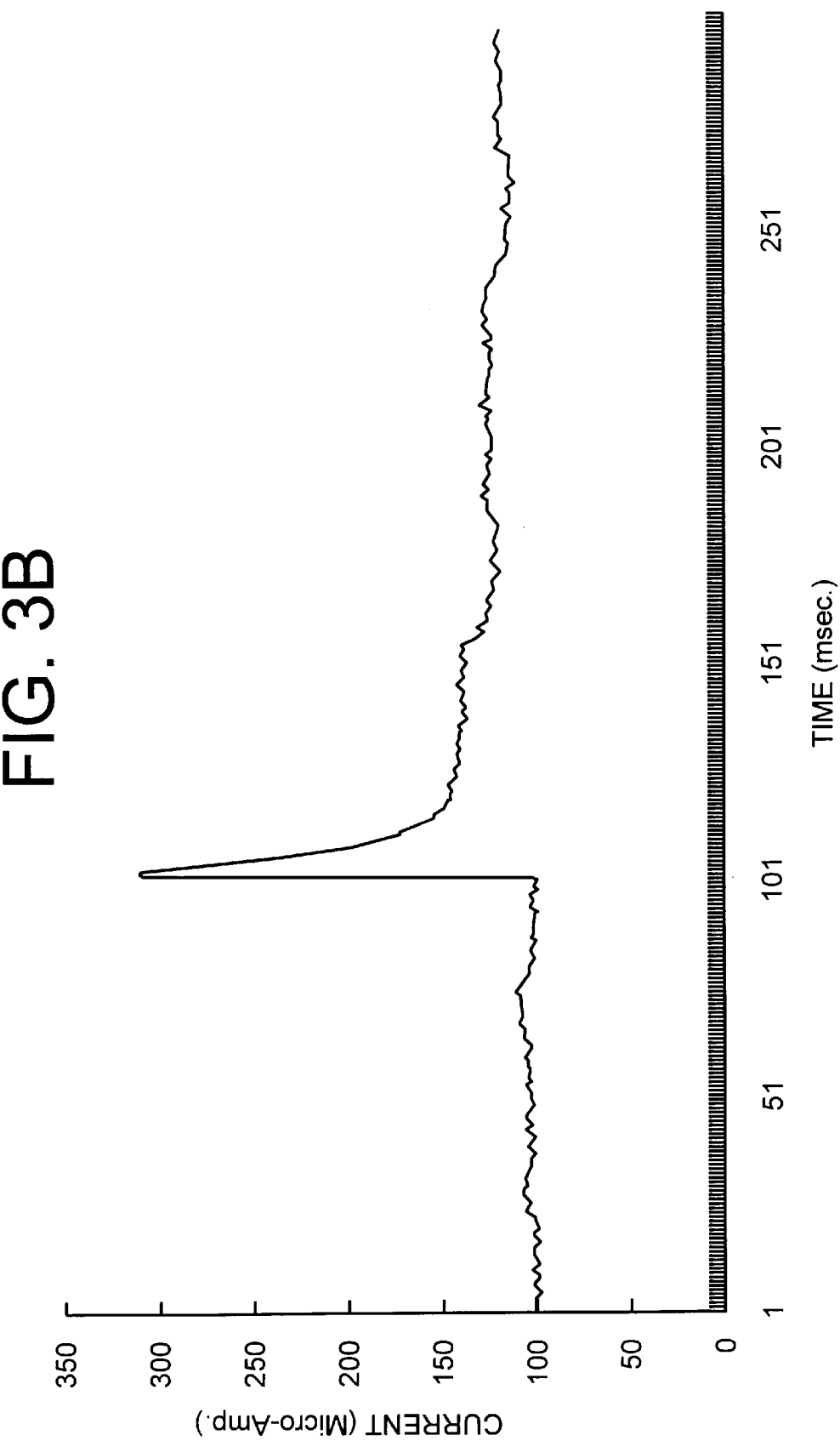

EXAMPLE:

A rat was anesthetized with Urethane and α Chloralose. One of its feet was flattened and attached to a copper plate (1 cm×0.5 cm×0.2 cm) with plenty of conducting gel (for EKG use) to ensure good conduction to the blood fluid. The other foot was penetrated with the needle electrode A. An impulse response was obtained as shown in FIG. 3A and then the rat's upper leg (near the heart end) was tied with a thread to block the blood circulation for 3 minutes, and then the needle electrode A was inserted into the rat's leg again. An impulse response was obtained as shown in FIG. 3B. When the thread tied to the rat's leg for 5 minutes was released and the needle electrode A was inserted into the rat's leg to measure the impulse response again, the result was the same as that shown in FIG. 3A. As compared with FIG. 2, this indicates that when the blood circulation is hindered, the lactate concentrated in the body fluid increases ~10 mole. This method can be used to study the body fluid in a biological body.

Figure 1:
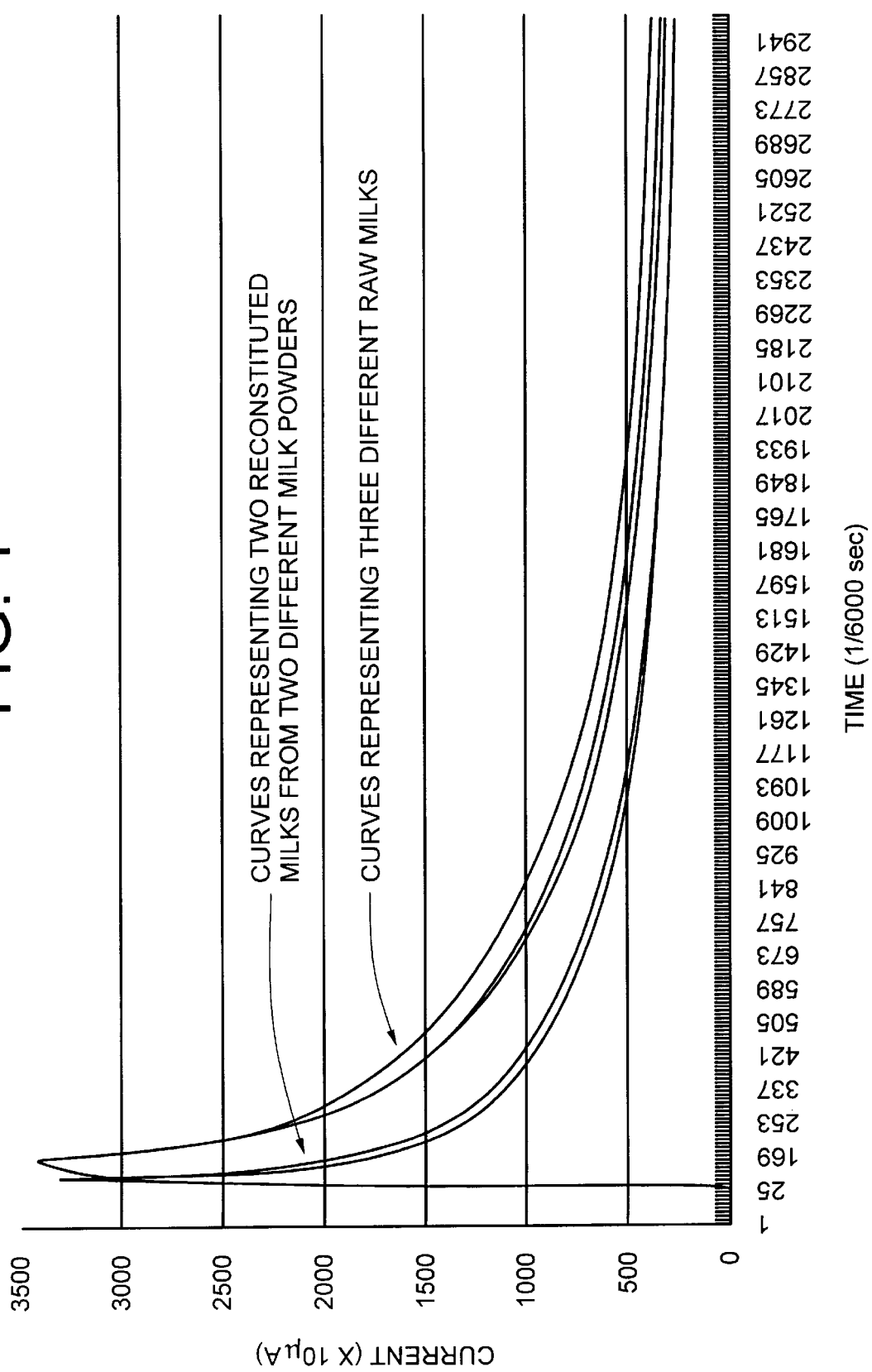
FIG. 1 is a graph illustrating the different curves based on the transient response used in accordance with the present invention and representing reconstituted milk and raw milk.

The present invention can be applied in conjunction with physical, chemical, biochemical and other analyses to analyze ingredients or compositions. The advantage of this method is that even if the chemical formulas are exactly the same, differences due to charge condition and particle size can still be distinguished by this method. For example, in the raw milk and the reconstituted milk from milk powder of FIG. 1, although the chemical formula of the milk powder is the same as that in the raw milk, the charged particles from the colloid have changed. The difference can be distinguished by the present method as viewed from FIG. 1 in which the two curves, representing two reconstituted milk samples from two different milk powders, are quite different from the three curves representing three different raw milk samples. With reference to FIG. 2, the concentrations of the Lactic Acid in solution e.g. 0.03, 0.01, 0.003 and 0.001M can be distinguished from each other by the curves drawn in accordance with this method. The other advantages of this method is that it is a simple, fast and cheap technique to detect charged particles in an aqueous solution.

Biological bodies, for example animals, plants, and human beings are composed mainly of aqueous solutions. It is therefore possible to analyze special ingredients in the body, such as ions, poison or other specific molecules. Lactate for example is an extraordinary ingredient which correlates with the oxygen supply when the glucose metabolic is normal. With sufficient glucose supply, the increase of the concentration of lactate in the tissue implies a the lack of oxygen or blood supply. Other specific charged particles such as poison or fragments from bacteria or viruses may also be detected if they have a specific impulse current.

FIG. 4 also illustrates an apparatus 10 for detecting the charged particles in an aqueous solution, formed in accordance with the present invention, which includes a pair of electrodes A and B, electrically connected to a dual relay 1 controlled by a program, an I/V converter 2, an inverted amplifier 3, an amplifier 4, an isolator 5, an A/D converter 6 and a data processor 7 (i.e. a personal computer). When the dual relay 1 is switched on by an analog signal 8 from the data processor 7, an exciting voltage 11 is applied between electrode B which contacts a biological body (e.g. a rat), and electrode A which is immersed in an aqueous solution in the biological body by a needle formed in a nail-like shape, to generate a current I. This current I is converted to voltage V (reverse) by the I/V converter 2, inverted amplifier 3 and amplifier 4. After amplification, the voltage 11 is then fed through the A/D converter 6 to generate a digital signal 12, to be fed to the data processor 7. The digital signal 12 is then analyzed in the data processor 7.

The data processor 7 generates an analog signal 8 in order to trigger the dual relay 1 to close. So the two electrodes connected to the potential source (in a preferred embodiment, this potential source is from the data processor 7) will supply a potential across the solution, because of the transient property of this current signal, the switch should close in less than 0. 1 ms. The sampling rate also should be higher than $10^{-4}$ sec (10K/sec) in order to give reliable data. This current signal is therefore converted into a digital signal by a current voltage conversion device, and the current-time curve is obtained by the data processor 7, and stored therein in order to be compared with the other standard data. The simplest way to analyze the data is to compare the shapes of the two curves directly. However, this may occupy too much memory space and reduce the efficiency of the comparison. Several criteria may be used to perform this current-time curve comparison.

(1) Peak-steady state ratio Peak means the largest value in the curves, while steady state means the value after the switch is closed for a few seconds (or within 10 ms. and the data value is not changed more than 5]

(2) Compare the values at Turning point—In mathematics term, compare point with $$\frac{d^2C}{dt^2} = 0$$

(wherein C represents the current-time curve)

(3) Compare value at a specific time interval—For example every 5 ms, 10 ms etc.

(4) Average value for every 1,000 data points

In actuality, any criteria currently used by EKG analysis can be used to analyze this current-time curve.

The current-time curve depends very much on the electrodes A and B, especially the electrode with the much smaller area of the two electrodes.

Also the electrode pair A and B need not be the same. However, to compare with other solutions, the same pair of electrodes A and B must be used. To be more precise, the one of the two electrodes that has the smaller area (larger resistance) must be the same. This is similar to any current measurement. In a series of resistances, the one with largest resistance determines the total resistance, especially when the resistance is hundreds of times larger than other resistances.

Therefore, in this measurement, the electrode A with much smaller area is in the form of a needle, while the reference electrode B has a much larger area of contact, and the transient current will be determined totally by the needle electrode A with the much smaller contact area, while the reference electrode B needs only to electrically contact the solution to form the current loop, because its response will not be seen in the current-time curve. The advantage of this design is especially useful when the solution is in a container which is not homogenous, for example a human body, since different parts of the body may contain different amounts of lactate. By using needle electrode A, the lactate content can be checked in a finger tip or in a small part of the liver, the small intestine etc. While the reference electrode B can be anywhere, (i.e., a hand or foot), the only requirement is that the reference electrode B must have a very large contact area with good conductivity (provided by gel or saline).

For an ordinary solution in a container, all that is required is a pair of electrodes to measure the testing solution, to use these electrodes again in the standard solution, and to compare the curve by the previous mentioned criteria. If the curves are the same, it means the two solutions are the same. If the curves are different same, it means the two solutions are not the.

To standardize the measurement, we need to provide needle electrode A with definite material and shape, and to be exposed to the solution with definite area, then the current-time curve will be reproducible. Then specific data can be set up, such as lactate in saline (e.g. in the biological body) as shown in FIG. 2, and each measurement may be compared with this stored data, so that the concentration of the lactate at that spot of the body (as shown in FIGS. 3A and 3B) may be estimated.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for detecting charged particles in an aqueous solution comprising the steps of:

(a) immersing a first electrode of an electrode pair in the aqueous solution to provide a conductive path between the aqueous solution and a second electrode of the electrode pair, wherein the second electrode is not immersed in the aqueous solution;

(b) applying a stepping potential through said electrode pair to measure an impulse current through the aqueous solution; and (c) comparing the impulse current with an impulse current of a reference solution having known ingredients to determine if the aqueous and the reference solutions are similar.

2. The method of claim 1, wherein the aqueous solution is within a biological body.

3. The method of claim 2, wherein one of said electrode pair includes a needle to penetrate tissue of the biological body to detect charged particles in the aqueous solution within the tissue.

4. The method of claim 2, wherein one of the known ingredients is lactate.

* * * * *